United States Patent [19]
Ray et al.

[11] Patent Number: 5,674,295
[45] Date of Patent: Oct. 7, 1997

[54] PROSTHETIC SPINAL DISC NUCLEUS

[75] Inventors: Charles D. Ray, Golden Valley; Eugene A. Dickhudt, New Brighton; Philip J. Ledoux, Stillwater; Beth A. Frutiger, Minneapolis, all of Minn.

[73] Assignee: RayMedica, Inc., Bloomington, Minn.

[21] Appl. No.: 638,306

[22] Filed: Apr. 26, 1996

Related U.S. Application Data

[63] Continuation of Ser. No. 324,142, Oct. 17, 1994, abandoned.

[51] Int. Cl.$^6$ .................................................. A61F 2/44
[52] U.S. Cl. ............................................................ 623/17
[58] Field of Search ........................... 623/8, 17; 606/61, 606/71

[56] References Cited

U.S. PATENT DOCUMENTS

| | | | |
|---|---|---|---|
| 3,867,728 | 2/1975 | Stubstad et al. | 3/1 |
| 3,875,595 | 4/1975 | Froning | 3/1 |
| 4,636,217 | 1/1987 | Ogilvie et al. | 623/17 |
| 4,772,287 | 9/1988 | Ray et al. | 623/17 |
| 4,904,260 | 2/1990 | Ray et al. | 623/17 |
| 4,932,969 | 6/1990 | Frey et al. | 623/17 |
| 5,047,055 | 9/1991 | Bao et al. | 623/17 |
| 5,171,280 | 12/1992 | Baumgartner | 623/17 |
| 5,192,326 | 3/1993 | Bao et al. | 623/17 |
| 5,246,458 | 9/1993 | Graham | 623/17 |
| 5,258,043 | 11/1993 | Stone | 623/66 |
| 5,306,307 | 4/1994 | Senter et al. | 623/17 |
| 5,306,308 | 4/1994 | Gross et al. | 623/17 |
| 5,306,309 | 4/1994 | Wagner et al. | 623/17 |

FOREIGN PATENT DOCUMENTS

| | | |
|---|---|---|
| 277282 | 10/1987 | European Pat. Off. . |
| 304305 | 5/1992 | European Pat. Off. . |
| 1015989 | 10/1952 | France . |
| 2639823 | 12/1988 | France . |
| 895433 | 1/1982 | U.S.S.R. . |
| 92010982 | 7/1992 | WIPO ....................... 623/17 |
| 94023671 | 10/1994 | WIPO ....................... 623/17 |

OTHER PUBLICATIONS

Clinical Efficacy and Outcome in the Diagnosis and Treatment of Low Back Pain, specifically Chapter 21, Charles Dean Ray. *The Artificial Disc, Introduction, History and Socioeconomics*, 1992, pp. 205–225.

*Primary Examiner*—Michael J. Milano
*Attorney, Agent, or Firm*—Kinney & Lange, P.A.

[57] ABSTRACT

An elongated, pillow shaped prosthetic spinal disc nucleus body for implantation into a human intervertebral spinal disc, made of a hydrogel core and a flexible constraining jacket surrounding the hydrogel material core that permits the hydrogel core to expand and contract. The hydrogel core has a length approximating the sagittal diameter of a nucleus of the human disc, a width less than the length, and a height less than the length or width. The hydrogel core will expand and contract in a desired fashion as it imbibes and expels fluids in response to various loads placed upon the spinal tract. The constraining jacket is porous to allow fluids to pass through to the hydrogel core, but prevents the hydrogel from escaping, thus fostering the natural physiology of the human intervertebral disc. By implanting two prosthetic spinal disc nucleus bodies side-by-side into a damaged disc of a human spine, both height and motion can be maintained.

23 Claims, 5 Drawing Sheets

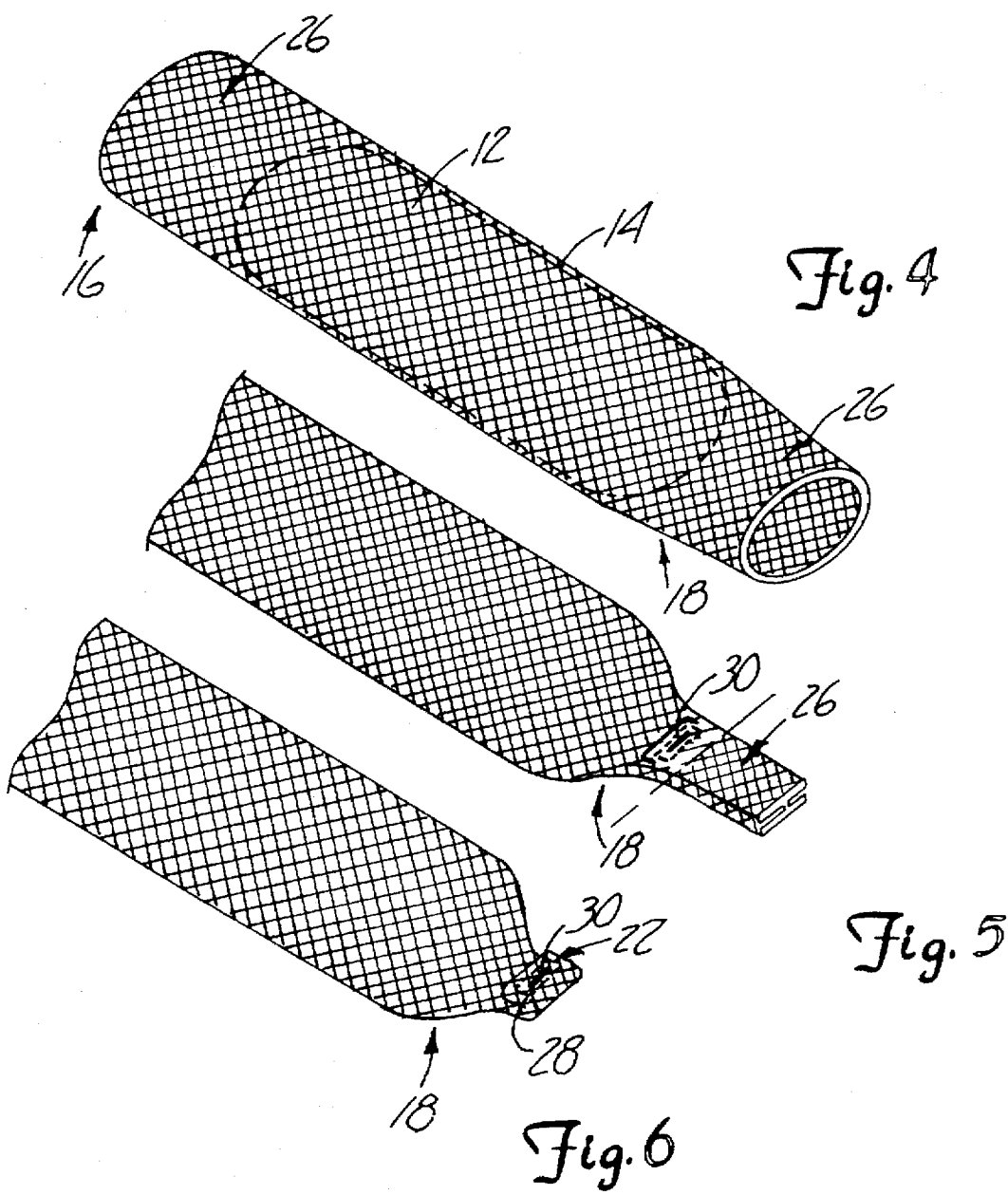

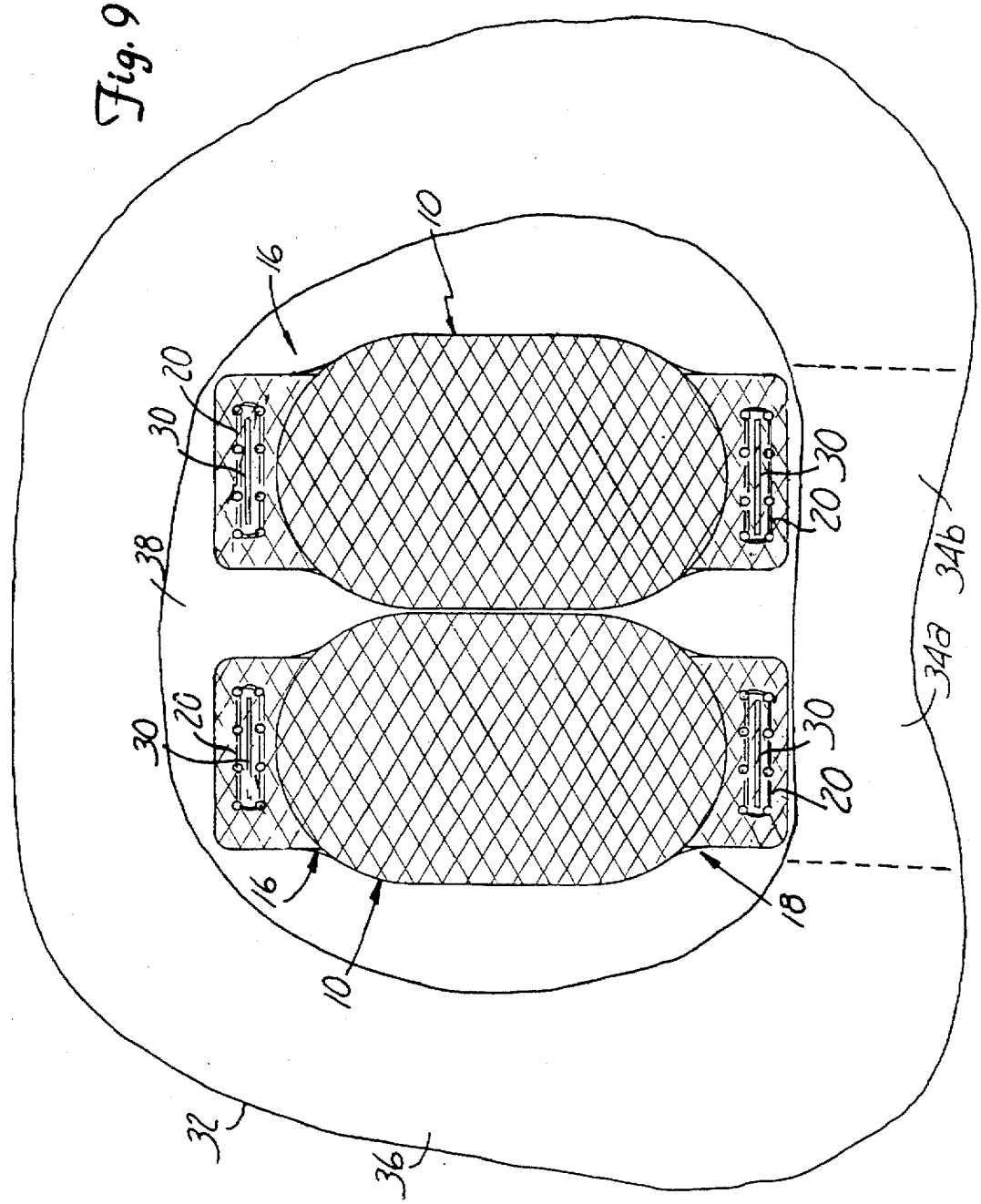

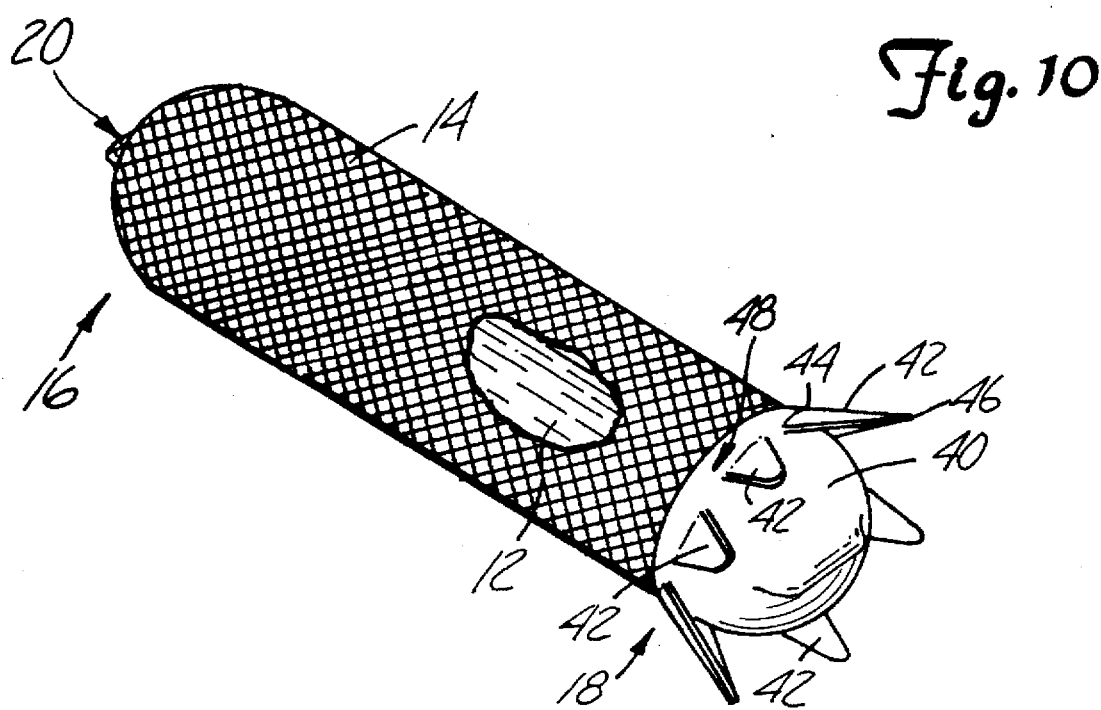

PROSTHETIC SPINAL DISC NUCLEUS

This is a contiuation of application Ser. No. 08/324,142, filed Oct. 17, 1994 now abandoned.

BACKGROUND OF THE INVENTION

Co-pending patent applications entitled "Spinal Anulus Cutter" and "Method For Surgical Implantation Of A Prosthetic Spinal Disc Nucleus" were filed on the same day as the present application and are assigned to the same assignee.

The present invention concerns a prosthetic spinal disc nucleus. More particularly it relates to an implantable capsule or pillow-shaped prosthetic discs nucleus having the ability to stimulate the resumption of the natural physiology of a degenerated human disc.

The vertebrate spine is the axis of the skeleton upon which all of the body parts "hang". In humans, the normal spine has seven cervical, twelve thoracic and five lumbar segments. The lumbar spine sits upon the sacrum, which then attaches to the pelvis, in turn supported by the hips and leg bones. The bony vertebral bodies of the spine are separated by intervertebral discs, which act as joints but allow known degrees of flexion, extension, lateral bending, and axial rotation.

The intervertebral disc primarily serves as a mechanical cushion between vertebral bones, permitting controlled motions within vertebral segments of the axial skeleton. The normal disc is a unique, mixed structure, comprised of three component tissues: the nucleus pulposus ("nucleus"), the anulus fibrosus ("anulus") and two vertebral end-plates. The two vertebral end-plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The anulus of the disc is a tough, outer fibrous ring which binds together adjacent vertebrae. This fibrous portion, which is much like a laminated automobile tire, is generally about 10 to 15 millimeters in height and about 15 to 20 millimeters in thickness. The fiber layers of the anulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The healthy nucleus is largely a gel-like substance having a high water content, and like air in a tire, serves to keep the anulus tight yet flexible. The nucleus-gel moves slightly within the anulus when force is exerted on the adjacent vertebrae while bending, lifting, etc.

The nucleus and the inner portion of the anulus have no direct blood supply. In fact, the principal nutritional source for the central disc arises from circulation within the vertebral body. Microscopic, villous-like fingerlings of nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into and released from the nucleus by cyclic loading. When fluid is forced out of the nucleus, it passes again through the end plates and then back into the richly vascular vertebral bodies. This cyclic loading amounts to daily variations in applied pressure on the vertebral column (body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the tightening and loosening effect stimulates normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal load cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the anulus to buckle in areas where the laminated plies are loosely bonded. As these overlapping laminated plies of the anulus begin to buckle and separate, either circumferential or radial anular tears may occur, potentially resulting in persistent and disabling back pain. Adjacent, ancillary spinal facet joints will also be forced into an overriding position, which may create additional back pain.

Whenever the nuclear tissue is herniated or removed by surgery, the disc space will narrow and may lose much of its normal stability. In many cases, to alleviate pain from degenerated or herniated discs, the nucleus is removed and the two adjacent vertebrae surgically fused together. While this treatment alleviates the pain, all discal motion is lost in the fused segment. Ultimately, this procedure places greater stresses on the discs adjacent to the fused segment as they compensate for the lack of motion, perhaps leading to premature degeneration of those adjacent discs. A more desirable solution would involve replacing in part or as a whole the damaged disc with a suitable prosthetic having the ability to complement the normal height and motion of a disc while mimicking the natural physiology of the disc.

The nutrition-flushing cycle of a natural disc is important for a prosthetic spinal disc nucleus to be successful. Vascular circulation and nerve supply to the disc is limited to the outer layers of the anulus, never penetrating more than a few millimeters or about five of the plies. Most of the nutrition of the inner anulus and nucleus is provided by diffusion through the end plates of the vertebral bodies and by the important pumping action between the partially loaded and fully loaded conditions of the disc. If the nutritional cycle is impeded, a variety of degenerative changes may occur. Nutrition to the inner disc slowly ceases, resulting in intradiscal build-up of acids and toxins, and other changes. This is followed by nuclear and anular fiber degeneration, shrinkage of the nucleus, segmental laxity, spur formation, disc space collapse, and perhaps spontaneous fusion. Additionally, significantly disabling back pain may develop.

Degenerated, painfully disabling interspinal discs are a major economic and social problem for patients, their families, employers and public at large. Any significant means to correct these conditions without further destruction, or fusion of the disc may therefore serve an important role. Other means to replace the function of a degenerated disc have major problems such as complex surgical procedures, which may require opening of the abdomen to install a large device that replaces the entire disc. Therefore, a substantial need exists for an easily implantable, prosthetic spinal disc nucleus having the ability to mimic the natural physiology of a human disc while restoring and maintaining the normal size of the disc space.

SUMMARY OF THE INVENTION

The invention provides an elongated, pillow-shaped prosthetic spinal disc nucleus body for implantation deep inside a human disc. The prosthetic body is composed of a hydrogel core, and a flexible constraining jacket surrounding the hydrogel core. These components reestablish near normal disc height and normal anulus position and function. Additionally, the prosthetic body will expand and contract in a primarily vertical direction, providing necessary support to the discal area, tightening and loosening the anulus in a normal, healthy manner. The components also work in concert to simulate the natural physiology of a human disc. In response to the removal and exertion of compressive loads, the prosthetic body will imbibe and expel fluids to promote the natural cyclic pumping of the discal area.

The hydrogel core has a length approaching the sagittal diameter of the nucleus of a natural disc, a width which is less than the length and is substantially constant over the length, and a height which is less than the length and width. The hydrogel core can imbibe and expel fluids. In a preferred embodiment, the hydrogel core has a water content of approximately 25-65% when fully hydrated. When imbibing and expelling fluids, the hydrogel core will expand and contract in the vertical dimension.

The hydrogel core of the present invention is surrounded by a constraining jacket. The constraining jacket is made of a flexible material which allows the hydrogel core to expand and contract in the vertical direction, while limiting simultaneous deformation in the horizontal direction of the frontal plane. The constraining jacket is porous and allows fluids to pass through as they are imbibed and expelled by the hydrogel core.

Once constructed, the prosthetic spinal disc nucleus body can be placed into the damaged disc space. According to a preferred embodiment, the prosthetic spinal disc nucleus body is implanted in pairs.

BRIEF DESCRIPTION OF THE DRAWINGS

FIGS. 4-6 illustrate steps of fabricating the prosthetic spinal disc nucleus body of FIG. 1.

FIG. 9 is a top, sectional view of a human disc space having two prosthetic spinal disc nucleus bodies implanted.

FIG. 10 is a perspective view of an alternative embodiment of the prosthetic spinal disc nucleus body which includes a tine assembly.

DETAILED DESCRIPTION OF THE PREFERRED EMBODIMENTS

Figure 1:
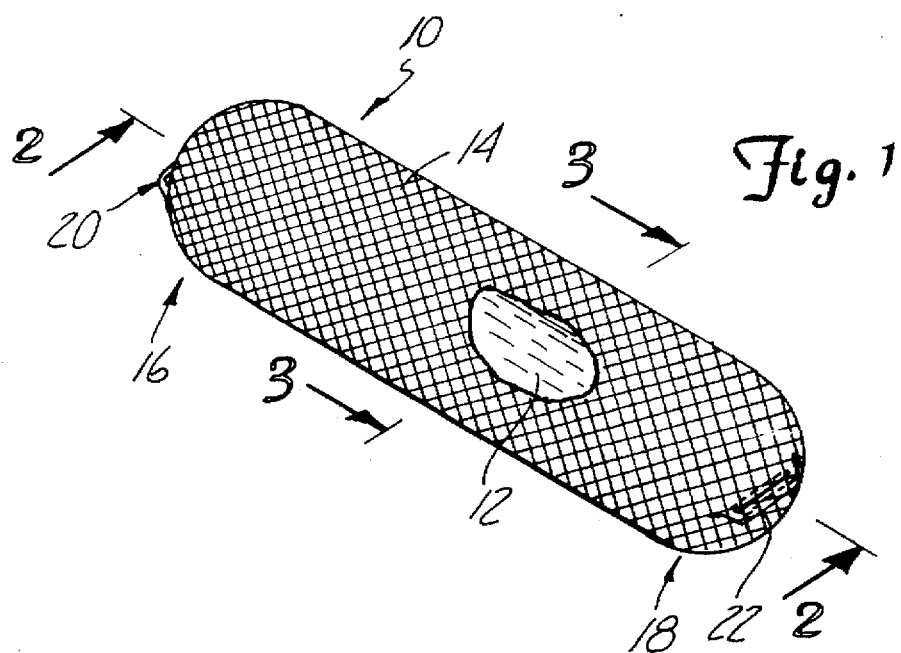
FIG. 1 is a perspective view of an elongated prosthetic spinal disc nucleus body, including a cutaway view showing a portion of a hydrogel material core, in accordance with the present invention.

A preferred embodiment of the prosthetic spinal disc nucleus body 10 is shown in FIG. 1. The prosthetic spinal disc nucleus body 10 is comprised of a hydrogel core 12 and a constraining jacket 14. The prosthetic spinal disc nucleus body 10 has an anterior end 16 and a posterior end 18. The constraining jacket 14 is secured around the hydrogel core 12 by an anterior closure 20 located at the anterior end 16 and a posterior closure 22 located at the posterior end 18.

Figure 2:
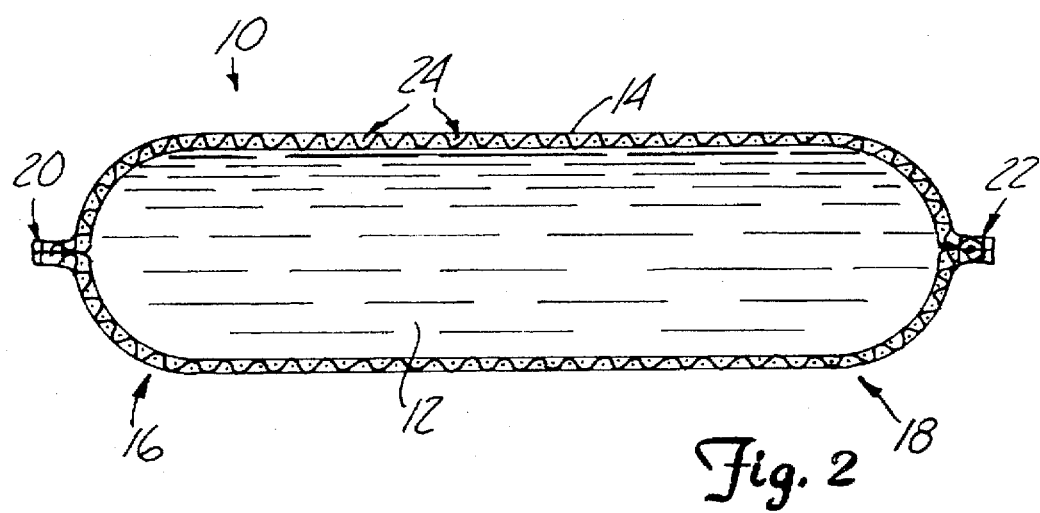
FIG. 2 is a side sectional view of the preferred prosthetic spinal disc nucleus body along the line of 2—2 of FIG. 1.
Figure 3:
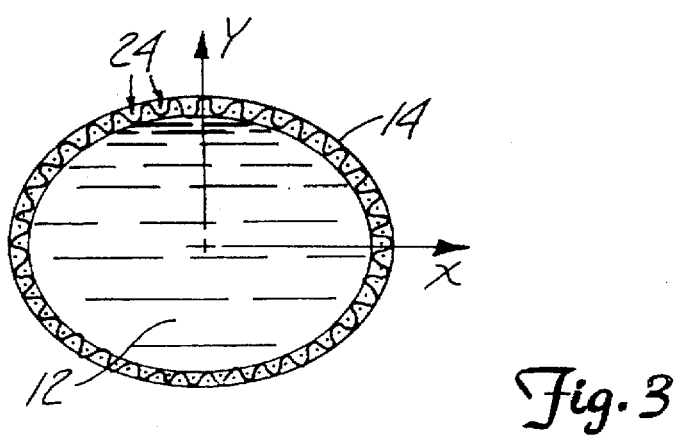
FIG. 3 is a frontal sectional view of the preferred prosthetic spinal disc nucleus body along the line 3—3 of FIG. 1.

As shown in FIGS. 2 and 3, the hydrogel core 12 is fabricated to assume a pillow shape. Along the longitudinal (or sagittal) plane (as shown in FIG. 2), the hydrogel core 12 has an around configuration whereas the frontal plane (as shown in FIG. 3) is oval.

The hydrogel core 12 is formulated as a mixture of hydrogel polyacrylonitrile. Alternatively, the hydrogel core 12 can be any hydrophilic acrylate derivative with a unique multiblock copolymer structure or any other hydrogel material having the ability to imbibe and expel fluids while maintaining its structure under various stresses. For example, the hydrogel core can be formulated as a mixture of polyvinyl alcohol and water. Much like a normal human nucleus, the hydrogel core 12 will swell as it absorbs fluids. The hydrogel core 12 has a time constant of swelling which is highly similar to that of the natural nucleus and will thus experience a 5-30% and preferably a 15-20% volume change depending on load over the course of 2-8 (preferably 4-8) hours. When fully hydrated, the hydrogel core 12 will have a water content of between 25-65%. The hydrogel material 12 of the preferred embodiment is manufactured under the trade name Hypan® by Hymedix International, Inc.

Completely surrounding the hydrogel core 12 is the constraining jacket 14. The constraining jacket 14 is preferably a closed tube made of a tightly woven high molecular weight, high tenacity polymeric fabric. Further, the constraining jacket 14 is flexible. In a preferred embodiment, high molecular weight polyethylene is used as the weave material for the constraining jacket 14. However, polyester or any other high molecular weight, high tenacity material can be employed. For example, carbon fiber yarns, ceramic fibers, metallic fibers, etc. are all acceptable.

The preferred woven construction of the constraining jacket 14 creates a plurality of small openings 24. These openings are large enough to allow bodily fluids to interact with the hydrogel core 12, which is maintained within the constraining jacket 14. However, the openings 24 are small enough to prevent the hydrogel 12 from escaping. Preferably, the openings 24 have an average diameter of about 10 micrometers, although other dimensions are acceptable. While the constraining jacket 14 is described as having a weave configuration, any other configuration having a semipermeable or porous attribute can be used.

By employing a flexible material for the constraining jacket 14, the hydrogel core 12 is allowed to expand and contract in a controlled fashion as it imbibes and expels fluids. When the hydrogel core 12 swells as a result of an influx of water, the constraining jacket 14 has sufficient flexibility to allow the hydrogel core 12 to expand. The strength and flexibility characteristics of the material used for the constraining jacket 14 are such that the pillow shape of the hydrogel 12 will always be maintained. By imparting a uniform constraining force on the surface of the hydrogel core 12, the constraining jacket 14 prevents undesired deformation of the prosthetic spinal disc nucleus body 10. However, for the prosthetic spinal disc nucleus body 10 to function as would a natural nucleus, some desired changes in the shape and size of the hydrogel core 12 must take place as loads are increased and decreased.

As fluids are imbibed, the woven constraining jacket 14 works in conjunction with the oval cross sectional shape of the hydrogel core 12 to control expansion of the hydrogel core 12. The prosthetic spinal disc nucleus body 10 initially assumes an oval shape in its frontal plane (as shown in FIG. 3). The nucleus body 10 will maintain this shape and act as a cushion against various loads placed upon it. As these loads are decreased (eg. when the patient reclines), the hydrogel core 12 imbibes surrounding fluids and expands. The constraining jacket 14 ensures that this expansion is only in the form of the hydrogel core 12 becoming more circular in frontal cross section. In other words, the constraining jacket 14 allows the hydrogel core 12 to expand in the y-direction (vertically), but prevents a simultaneous expansion in the x-direction (horizontally). Further, while limited horizontal contraction will preferably occur, the vertical expansion proceeds at a proportionately greater rate than the horizontal contraction. Therefore, the smaller the load placed upon the prosthetic spinal disc nucleus body 10, the closer the body 10 is to a circular frontal cross section. To help achieve this unique effect, the preferred constraining jacket 14 is substantially inelastic. To prevent the hydrogel core 12 from escaping, the constraining jacket 14 has a burst strength which is greater than the swelling pressure of the hydrogel core 12 when fully hydrated.

FIGS. 4-6 illustrate the manufacturing of the prosthetic spinal disc nucleus body 10. First, the hydrogel core 12 is formulated. An appropriately sized volume of hydrogel material is dehydrated, resulting in an undersized, substantially cylindrical gel capsule. This dehydrated hydrogel material 12 is then inserted into the constraining jacket 14.

As shown in FIG. 4, the constraining jacket 14 is preferably tubular in shape with openings at both the anterior end 16 and the posterior end 18. The dehydrated hydrogel material 12 is placed within the constraining jacket 14 and centered between the anterior end 16 and the posterior end 18. The ends of the constraining jacket 14 are then secured by forming the anterior closure (not shown) and the posterior closure 22.

In the centered position, the hydrogel material core 12 will have a length smaller than that of the constraining jacket 14, resulting in excess outer layer material 26 at both the anterior end 16 and the posterior end 18. The excess outer layer material 26 at both the anterior end 16 and the posterior end 18 is closed to prevent the hydrogel material 12 from escaping or leaking from the confines of the constraining jacket 14. As shown in FIGS. 5 and 6, to form the posterior closure 22, the excess outer layer material 26 is preferably folded or tucked and then closed. The fold is created by pinching two opposing sides of the excess material 26 centrally towards one another, approximating a "FIG. 8" form. The two remaining free ends are flattened against one another, resulting in an "H-shaped" fold as shown in FIG. 5.

The fold is then closed by sewing a dense, bar-tack stitch 28 across the folded section at a position near the hydrogel core 12. The bar-tack stitch 28 material is preferably the same high tenacity polymeric material, such as high molecular weight polyethylene, as is used for the constraining jacket 14. By employing the same material for both the constraining jacket 14 and the bar-tack stitch 28, the biocompatibility of the entire prosthetic spinal disc nucleus body 10 is ensured. The remaining excess material 26 is removed by a thermal cut made at a point distal to the bar-tack stitch 28. This thermal cut fuses the potentially fraying ends of the jacket, distal to the stitched portion 28.

While FIGS. 5 and 6 only show the posterior closure 22 on the posterior end 18, the excess material 26 on the anterior end 18 is folded and sealed in a similar fashion to form the anterior closure 20. Notably, it is not always necessary to fold the excess outer layer material 26, where the anterior end 16 and the posterior end 18 are simply sealed by the dense, bar-tack stitch 28 without folding the material 26. Further, while the constraining jacket 14 has been described as having two openings, it may instead be manufactured with a single opening, either on an end or side, through which the hydrogel core 12 is inserted.

To aid in ensuring proper placement of the prosthetic spinal disc nucleus body 10 within the intervertebral disc space and to review the stability of the prosthetic disc body 10 during patient follow-ups, a radiopaque wire 30 is placed inside the constraining jacket 14, at either the anterior end 16 or the posterior end 18, or both or longitudinally along the length of the constraining jacket 14. The radiopaque wire 30 is visible in x-ray applications and is preferably made of a platinum-iridium material, but can be any other material having a radiopaque and biologically inert characteristics. The wire 30 is placed within the excess material 26 at the anterior end 16 or the posterior end 18 and is secured by the bar-tack stitch 28. Alternatively, a radiopaque thread can be woven into the constraining jacket 14 or a radiopaque material can be added to the hydrogel core 12.

In its final form, the prosthetic spinal disc nucleus body 10 will have lengths of about 15 to 25 millimeters and an outer diameter of about 6 to 15 millimeters. The preferred disc body 10 is 25 millimeters in length and 10 millimeters in outer diameter. These dimensions conform with the approximate length of the sagittal diameter and approximate height of an adult human disc nucleus space, respectively. It is realized that not all human discs are of the same size. Therefore, the prosthetic spinal disc nucleus body 10 alternatively is constructed to assume dimensions of 20 millimeters in length and 10 millimeters in outer diameter; 25 millimeters in length and 7 millimeters in outer diameter; and 20 millimeters in length and 7 millimeters in outer diameter. Notably, other sizes are possible. The appropriate prosthetic disc for a particular patient is determined by various diagnostic procedures prior to and during surgery. Basically, the properly dimensioned prosthesis is a function of the patient's size and spinal level. By providing prosthetic spinal disc nucleus bodies 10 with varying dimensions, the space requirements reflected by any spinal segment, human or animal, are satisfied.

Following closure of the constraining jacket 14 about the hydrogel core 12, the prosthetic spinal disc nucleus body 10 is rehydrated and then subjected to compressive loads or "conditioned". The conditioning amounts to a series of at least three compressive loads being applied across the length of the prosthetic body 10. The magnitude of in vivo compressive loads will vary from patient to patient and is a function of the patient's size and spinal level. For example, published literature has stated that the normal sitting or standing compressive load on the discal area is 1.8 multiplied by the patient's body weight. Further, the maximum compressive load placed upon the lumbar discal area during usual, daily activities is 3.6 multiplied by the patient's body weight. The conditioning, therefore, will consist of a series of compressive loads being placed upon the prosthetic body 10 equivalent to a minimum of 1.8 multiplied by the typical body weight up to a maximum of 3.6 multiplied by the typical body weight. Following conditioning, the hydrogel core 12 will consistently return to its desired shape and size following the application and removal of compressive loads.

As a further benefit, the hydrogel 12 and its manufacturing process place volume expansion constraints on the hydrogel 12. Even if the hydrogel 12 were unconstrained (eg. if the constraining jacket 14 ruptures), following conditioning the hydrogel 12 will not expand to more than about twice its volume after conditioning. Thus, a continuous, unlimited, potentially hazardous swelling of the hydrogel 12 will not occur should the constraining jacket 14 be disrupted. This internalized constraint will also prevent possible over expansion of the hydrogel core 12 if the prosthetic discal body 10 is continually unloaded in the disc space or if the prosthetic discal body 10 were to be displaced into another body cavity such as the spinal canal or abdomen.

The conditioning renders the prosthetic spinal disc nucleus body 10 to a partially flattened or oval shape. For example, a prosthetic body 10 originally having a diameter of about 10 millimeters will have a height of about 7 millimeters and a width of about 14 millimeters following conditioning. Similarly, conditioning will alter a prosthetic body 10 having an original diameter of about 7 millimeters to one having a height of about 5 millimeters and a width of about 12 millimeters. The conditioned prosthetic spinal disc nucleus body 10 is then inserted into a retaining tube to maintain this oval shape up until implantation. The retaining tube is preferably made of implantable grade stainless steel, but can be any other surgically safe material such as polyethylene. The prosthesis 10 and its retaining tube may be packaged, surrounded by sterile water, saline or physiological solution (Ringer's). The entire surgical package is sterilized in a tray, via gamma, steam or other type of sterilization. Once conditioned, retained, and sterilized, the prosthetic spinal disc nucleus body 10 is ready for implantation into the human disc space.

Figure 7:
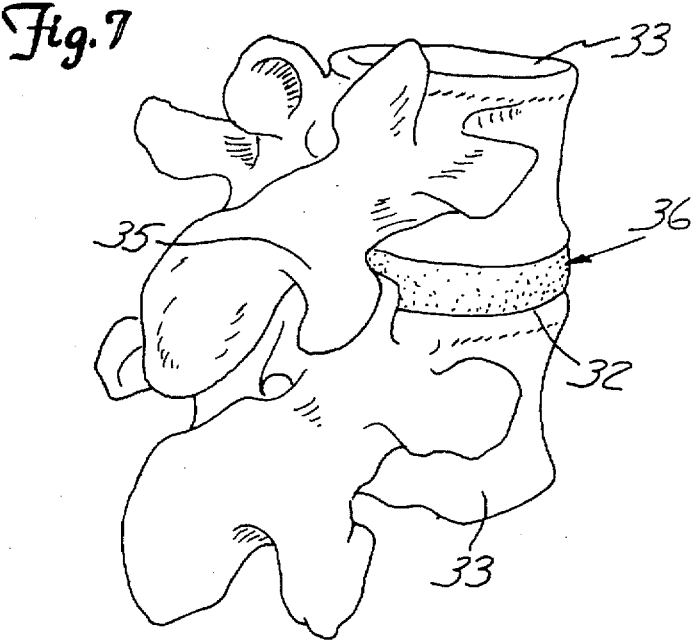
FIG. 7 is a perspective view of a spinal segment including a degenerated discal area.
Figure 8:
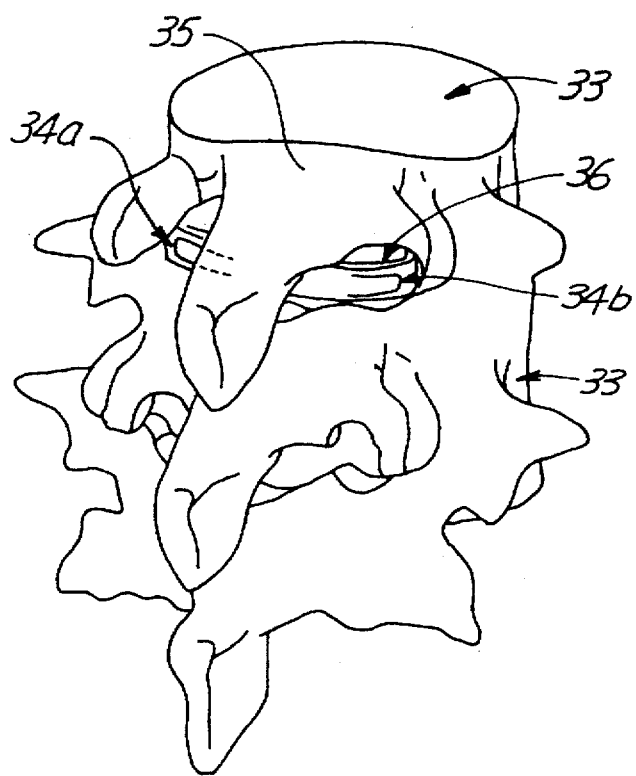
FIG. 8 is a posterior view of a human spine showing two flaps that have been cut through an anulus.

As shown in FIGS. 7, 8 and 9, the final prosthetic spinal disc nucleus body 10 is preferably inserted in pairs into a damaged disc space 32. The disc space 32 separates two adjacent vertebrae 33. Proper positioning is achieved by first performing a bilateral laminotomy in a targeted lamina area 35. A pair of flaps 34a and 34b are created in the anulus 36 and any excess material, such as the nucleus 38, necessary to create room for the prosthetic spinal disc nucleus body 10 is removed. The flaps 34a and 34b preferably have a height less than the height dimension of the prosthetic spinal disc nucleus body 10. In a preferred embodiment, the flaps 34a and 34b have a length of about 12 millimeters and a height of about 6 millimeters for use with a prosthetic body having a height of 7 millimeters. The vertebrae 33 adjacent to the damaged disc 32 are slightly separated to allow for the implantation.

This slight separation is achieved by inserting an inflatable jack through one of the flaps 34a or 34b and jacking apart the adjacent vertebrae 33. Once separation sufficient to insert a nucleus body 10 is achieved, the flap 34a or 34b not occupied by the jack has a prosthetic spinal disc nucleus body 10 inserted via a tapered holding tube. The jack is then deflated and removed, and a second prosthetic spinal disc nucleus body 10 is placed through the remaining flap 34a or 34b. To promote an increase in hydration, saline or similar fluid is injected or flushed into the nucleus area 38. When properly implanted, the anterior end 16 of each prosthetic spinal disc nucleus body 10 will be adjacent to and inside of the anterior end of the anulus 36; the posterior end 18 will be adjacent to and inside of the posterior end of the anulus 36. By imparting the flaps 34a and 34b with a height dimension smaller than that of the body 10 and closing the flaps 34a and 34b after implant, a positive fixation within the anulus 36 is provided and likewise the retropulsion of the discal nucleus 10 from the anulus 36 is prevented.

Following implantation, the prosthetic spinal disc nucleus bodies 10 function as intervertebral spacer, a cushion and fluid pump. As previously described, the prosthetic spinal disc nucleus body 10 has an oval shaped frontal cross section. As fluids are imbibed (via the absence, or removal, of loads upon the spinal tract), the hydrogel core 12 begins to swell. The constraining jacket 14 forces the hydrogel core 12 to become more circular in frontal cross section by allowing the frontal height to expand while preventing an increase in width. Instead, as the height expands, the width preferably will slightly contract. In this regard, the height of the hydrogel core 12 changes at a proportionately greater rate than the width changes. This controlled swelling effectively pushes or further separates the vertebrae 33 adjacent to the disc space apart, as would a normal nucleus.

Conversely, as loads on the spinal tract increase, the prosthetic spinal disc nucleus body 10 cushions the adjacent vertebrae 33 and slowly contracts in the frontal plane as the hydrogel core 12 releases or "pumps out" fluids and thus flushes out the accumulated acids or autotoxins contained therein. During this pumping action, the constraining jacket 14 forces a vertical contraction while preventing a horizontal contraction. Notably, some expansion in the horizontal plane will occur. The height of the prosthetic spinal disc nucleus body 10 contracts at a proportionately greater rate than the width expands. The hydrogel core 12 thus becomes more oval shaped in cross section and loses volume as compressional loads are placed upon the discal area. Notably, the constraining jacket 14 of the present invention independently absorbs the force/pressure of the hydrogel core 12 as it expands and contracts. Thus, the anulus 36 is not required to support the force/pressure from the hydrogel core 12.

In an alternative embodiment shown in FIG. 10, to assist in preventing the retropulsion or dislocation of the prosthetic spinal disc nucleus body 10 after implant from the nucleus (38 in FIG. 9) back through the flap (34a or 34b in FIG. 9) in the anulus (36 in FIG. 9), the prosthetic body 10 can be provided with a tine assembly 40 located on the external surface of the prosthetic body 10. When properly oriented, the tine assembly 40 will promote the simple implantation of the prosthetic body into the disc space, but greatly inhibits removal or spontaneous retropulsion. The tine assembly 40 provides an additional fixation of the prosthetic spinal disc nucleus within the disc space.

The tine assembly 40 is attached to the posterior end 18 of the prosthetic spinal disc nucleus body 10 and projects away from the external face of the constraining jacket 14. Each individual tine 42 on the tine assembly 40 has an approximately triangular shape, including a base 44 and an end 46. The base 44 of each tine 42 is integrally attached to a frame 48 of the tine assembly 40. Each tine 42 projects laterally away from the tine assembly frame 48 in an angular fashion. In other words, when the tine assembly 40 is properly oriented on the prosthetic spinal disc nucleus body 10, each individual tine 42 projects away from the constraining jacket 14 in a direction rearward with respect to the anterior end 16 and outward with respect to the posterior end 18.

The tine assembly 40 is preferably made of the same high molecular weight, high tenacity polymeric material, such as polyethylene, as is used for the constraining jacket 14. By employing a material of this type, the tine assembly 40, and therefore each individual tine 42, will have the desired strength and flexibility characteristics required for proper implantation of the prosthetic spinal disc nucleus body 10. Prior to and during implant, the tine 42 material has sufficient flexibility to allow each tine 42 to fold down against the external surface of the constraining jacket 14. When implanted, the tine 42 material has a resiliency which forces each tine 42 to assume the angular position shown in FIG. 10. In this expanded position, each tine 42 has a strength characteristic which will prevent the retropulsion of the prosthetic spinal disc nucleus body 10 from its final implantation position and provides a positive fixation within the anulus.

The tine assembly 40 has been described as preferably having individual tine bodies 42 extending from the frame 48. Each tine 42 is equally spaced from one another, providing uniform support to the prosthetic spinal disc nucleus body 10 when placed within the anulus. However, any number or configuration of tines 42 can be used which also provide a solid fixation within the anulus and prevent retropulsion.

During manufacture, once the anterior closure 20 and the posterior closure 22 have been formed, the tine assembly 40 is attached to the prosthetic spinal disc nucleus body 10. The tine assembly 40 is slid over the posterior end 18 and secured to the constraining jacket 14 by frictional or mechanical fastening or sewing, which may include a hook and loop configuration, or adhesive.

An additional means for retarding expulsion is the potential use of tapered collars secondarily attached to the constraining jacket 14 by way of sewing or spin entanglement. Such collars would collapse against the jacket 14 on insertion of the prosthetic spinal disc nucleus body 10 and flare on attempted removal or forceful expulsion from the anular confines.

By providing a small, pillow-shaped body having the distinct ability to imbibe and expel fluids, the discal nucleus body of the present invention: a) restores the height of the damaged disc space, b) restores and tightens the natural anulus to stop further degeneration and permit its healing, c) restores the normal load-unload cycling and thus flushes out toxic by-products, bringing in fresh nutrients to the nucleus and anulus, d) allows a near normal range of motion, e) relieves the movement-induced discogenic pain of the vertebral segment, and f) allows the use of a minimal, posterior surgical procedure that provides both cost and medical benefits. The device of the present invention can be implanted with a high degree of certainty that the required dimensions presented by the damaged disc space will be maintained following insertion of the discal nucleus device.

Although the present invention has been described with reference to preferred embodiments, workers skilled in the art will recognize that changes may be made in form and detail without departing from the spirit and scope of the invention. For example, other methods of sealing the ends of the constraining jacket exist such as heat, ultrasound, crimp ring seals or spin entanglement. Additionally, more than a single layer of material may be used to maintain the integrity of the hydrogel core. In other words, a plurality of constraining jackets can surround the hydrogel material which act in concert to allow fluids to be imbibed and expelled while maintaining the pillow shape of the hydrogel core.

The hydrogel itself can have an outer "skin" formed by ion implantation which causes outer layer polymerization and functions as the constraining jacket or as an interposed membrane between the gel mass and the jacket. Alternatively, while the above-described expansion and contraction of the hydrogel core is achieved via the use of a constraining jacket, other means exist for limiting expansion and contraction in the width of the hydrogel core without the use of a separate constraining jacket. For example, a truss can be embedded along the sides of the hydrogel core. The truss is perpendicular to the width of the hydrogel core and effectively creates an anisotropic scenario in which the hydrogel core is allowed to expand solely in height when imbibing fluids. Similarly, the hydrogel core will contract only in height when expelling fluids. Other tine or circumferential collar configurations exist which act to prevent retropulsion of the discal body and can be located at any other position along the discal body, including the anterior end. Finally, the prosthetic spinal disc nucleus body can be used in all areas of the spine, and can be implanted in animals, such as in the disc space of a dog or the ankle of a horse.

What is claimed is:

1. A prosthetic disc nucleus for implantation into a human spinal disc having a nucleus area defined generally in a horizontal plane by an anulus and generally in a vertical plane by two vertebral end plates, the nucleus area having a sagittal diameter and a traverse diameter, the prosthetic disc nucleus comprising:

a hydrogel core having a length approximating the sagittal diameter of the nucleus area and a width less than half of the transverse diameter of the nucleus area, wherein the hydrogel core is configured such that it will consistently return to a predetermined shape following removal of a load; and a jacket surrounding the hydrogel core, wherein the jacket is configured to have a horizontal limit in the horizontal plane of the nucleus area such that the jacket directs expansion of the hydrogel core to only the vertical plane of the nucleus area after expansion of the hydrogel core reaches the horizontal limit of the jacket.

2. The prosthetic disc nucleus of claim 1 wherein the predetermined shape is an oval frontal cross-section.

3. The prosthetic disc nucleus of claim 1 wherein the hydrogel core is subjected to a plurality of compressive forces prior to implant to render the hydrogel core to the predetermined shape.

4. The prosthetic disc nucleus of claim 1 wherein the hydrogel core is dehydrated prior to implantation and hydrated after implantation, and further wherein the hydrogel core constrained by the jacket is configured to expand predominately in height upon hydration.

5. The prosthetic disc nucleus of claim 1 wherein the hydrogel core is dehydrated prior to implantation and hydrated after implantation, and further wherein the jacket is configured to direct the hydrogel core to expand in the vertical plane upon hydration.

6. The prosthetic disc nucleus of claim 5 wherein the jacket is substantially inelastic for directing the hydrogel core to expand in the vertical plane upon hydration.

7. The prosthetic disc nucleus of claim 1 wherein the hydrogel core has a water content of 25–65% when fully hydrated.

8. The prosthetic disc nucleus of claim 1 wherein the jacket is a woven tube.

9. The prosthetic disc nucleus of claim 1 wherein the jacket has openings which permit fluids to pass through the jacket to the hydrogel core while blocking passage of the hydrogel core out of the jacket.

10. The prosthetic disc nucleus of claim 1 wherein the jacket is made of a high molecular weight, high tenacity material.

11. The prosthetic disc nucleus of claim 1 wherein the jacket is woven tube having two ends and wherein at least one end has a closure.

12. The prosthetic disc nucleus of claim 1, further including: radiopaque material within the jacket.

13. The prosthetic disc nucleus of claim 1, further including:

means for maintaining the prosthetic disc nucleus within the disc area following implant, wherein the means for maintaining is attached to the jacket.

14. A prosthetic disc nucleus for implantation into a human spinal disc having a nucleus area defined by an anulus, the nucleus area having a sagittal diameter and a transverse diameter, the prosthetic disc nucleus comprising:

a hydrogel core having a cylindrical body and a frontal cross-section which is a flattened oval, wherein the flattened oval cross-section defines a major axis and a minor axis; and a jacket surrounding the hydrogel core, wherein the jacket is configured to have a horizontal limit in a plane defined by the major axis of the hydrogel core such that the jacket directs expansion of the hydrogel core to only the minor axis of the hydrogel core after expansion of the hydrogel core reaches the horizontal limit of the jacket.

15. The prosthetic disc nucleus of claim 14 wherein the frontal cross-section of the hydrogel core has a height which is less than a height of the anulus.

16. The prosthetic disc nucleus of claim 14 wherein the hydrogel core is in a dehydrated state prior to implantation and is in a fully hydrated state after implantation, and further wherein the fully hydrated hydrogel core constrained by the jacket is configured to provide a natural disc space height.

17. The prosthetic disc nucleus of claim 1 wherein the hydrogel core swells from the dehydrated state to the fully hydrated state, and further wherein the hydrogel core is configured to swell with enough to force to restore natural disc height.

18. A prosthetic disc nucleus for implantation into a human spinal disc having a nucleus area with a generally horizontal plane, a sagittal diameter and a transverse diameter defined by an anulus, and a generally vertical plane defined by two vertebral end plates, the prosthetic disc nucleus comprising:

a hydrogel core having a length approximating the sagittal diameter of the nucleus area and a width less than half of the transverse diameter of the nucleus area, wherein the hydrogel core is dehydrated prior to implantation and hydrated after implantation and the hydrogel core is configured such that it will maintain a predetermined shape after hydration; and a jacket surrounding the hydrogel core, wherein the jacket is configured to have a horizontal limit in the horizontal plane of the nucleus area such that the jacket directs expansion of the hydrogel core to only the vertical plane of the nucleus area after expansion of the hydrogel core, reaches the horizontal limit of the jacket.

19. A prosthetic disc nucleus for implantation into a human spinal disc having a nucleus area defined by an anulus, the nucleus area having a sagittal diameter and a transverse diameter, the prosthetic disc nucleus comprising:

a hydrogel core having a length approximating the sagittal diameter of the nucleus area, a width less than half of the transverse diameter and a frontal cross-section which is a flattened oval having a major axis and a minor axis, wherein the hydrogel core has a water content of 25–65% when fully hydrated and is subjected to a plurality of compressive cycles prior to implantation so that the hydrogel core is configured such that it will consistently return to a predetermined shape following removal of a load; and a substantially inelastic woven tube surrounding the hydrogel core, wherein the woven tube is configured to have a horizontal limit in a plane defined by the major axis of the hydrogel core such that the jacket directs expansion of the hydrogel core to only the minor axis of the hydrogel core after expansion of the hydrogel core reaches the horizontal limit of the jacket.

20. A method of manufacturing a prosthetic disc nucleus for implantation into a human disc having a nucleus area defined by an anulus, the nucleus area having a sagittal diameter and a transverse diameter, the method including:

forming a cylindrical hydrogel core having a flattened oval-shaped frontal cross-section which defines a major axis and a minor axis;

forming a woven jacket having a limit in a plane defined by the major axis of the hydrogel core, wherein the jacket is configured to direct expansion of the hydrogel core only to a direction defined by the minor axis once expansion of the hydrogel core reaches the limit of the jacket;

inserting the hydrogel core into an open end of the woven jacket; and closing the open end of the woven jacket to surround the hydrogel core.

21. The method of manufacturing of claim 20, further including: hydrating the hydrogel core after insertion into the woven jacket.

22. The method of manufacturing of claim 20, further including:

subjecting the hydrogel core to a plurality of compressive loads prior to implant.

23. The method of manufacturing of claim 20 wherein the hydrogel core has a length approximating the sagittal diameter and a width which is less than half of the transverse diameter.

* * * * *